US00PP17286P2

(12) United States Plant Patent
Gitzels

(10) Patent No.: US PP17,286 P2
(45) Date of Patent: Dec. 19, 2006

(54) ***DAHLIA* PLANT NAMED 'BALDELHON'**

(50) Latin Name: *Dahlia variabilis*
Varietal Denomination: Baldelhon

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 32 days.

(21) Appl. No.: 11/298,056

(22) Filed: Dec. 9, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
*Assistant Examiner*—Annette H Para
(74) *Attorney, Agent, or Firm*—Audrey Charles

(57) ABSTRACT

A new and distinct cultivar of *Dahlia* plant named 'Baldelhon' characterized by its light red and orange-bicolored flowers, medium green-colored foliage, good basal branching character, and moderately vigorous, upright growth habit.

2 Drawing Sheets

Latin name of genus and species of plant claimed: *Dahlia variabilis*.
Variety denomination: 'Baldelhon'.

BACKGROUND OF THE INVENTION

The present invention relates to a new and distinct cultivar of *Dahlia* plant botanically known as *Dahlia variabilis* and hereinafter referred to by the cultivar name 'Baldelhon'.

The new cultivar originated in a controlled breeding program in Rijsenhout, the Netherlands during May 2002. The objective of the breeding program was the development of freely flowering *Dahlia* cultivars with large flowers and a moderately vigorous growth habit.

The female (seed) parent of the new cultivar was the proprietary *Dahlia variabilis* breeding selection designated 1151, not patented, characterized by its white-colored ray florets and upright growth habit. The male (pollen) parent of the new cultivar was 'Dapasuje', U.S. Plant patent application Ser. No. 11/168,196, characterized by its deep red and orange bicolored ray florets and compact growth habit. The new *Dahlia* was discovered and selected by the inventor as a single flowering plant within the progeny of the above stated cross-pollination during May 2003 in a controlled environment at Rijsenhout, the Netherlands.

Asexual reproduction of the new cultivar by terminal stem cuttings since May 2003 at Rijsenhout, the Netherlands and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Baldelhon' as a new and distinct cultivar of *Dahlia* plant:

1. Light red and orange-bicolored flowers;
2. Medium green-colored foliage;

3. Good basal branching character; and
4. Moderately vigorous, upright growth habit.

Plants of the new cultivar differ from plants of the female parent primarily in flower color and from plants of the male parent primarily in flower color and growth habit.

Of the many commercially available *Dahlia* cultivars known to the inventor, the most similar in comparison to the new cultivar is 'Baldelemz', U.S. Plant Pat. No. 16,448. However, in side by side comparisons, plants of the new cultivar differ from plants of 'Baldelemz' in the following characteristics:

1. Plants of the new cultivar are more compact than plants of 'Baldelemz';
2. Plants of the new cultivar have smaller inflorescences than plants of 'Baldelemz'; and
3. Plants of the new cultivar have a different flower color from plants of 'Baldelemz'.

BRIEF DESCRIPTION OF THE PHOTOGRAPHS

The accompanying photographs show, as nearly as true as it is reasonably possible to make the same in color illustrations of this type, typical flower and foliage characteristics of the new cultivar. Colors in the photographs differ slightly from the color values cited in the detailed description, which accurately describes the colors of 'Baldelhon'. The plants were grown in 10 cm pots for 9 weeks in a greenhouse at West Chicago, Ill.

DETAILED BOTANICAL DESCRIPTION

Figure 1:
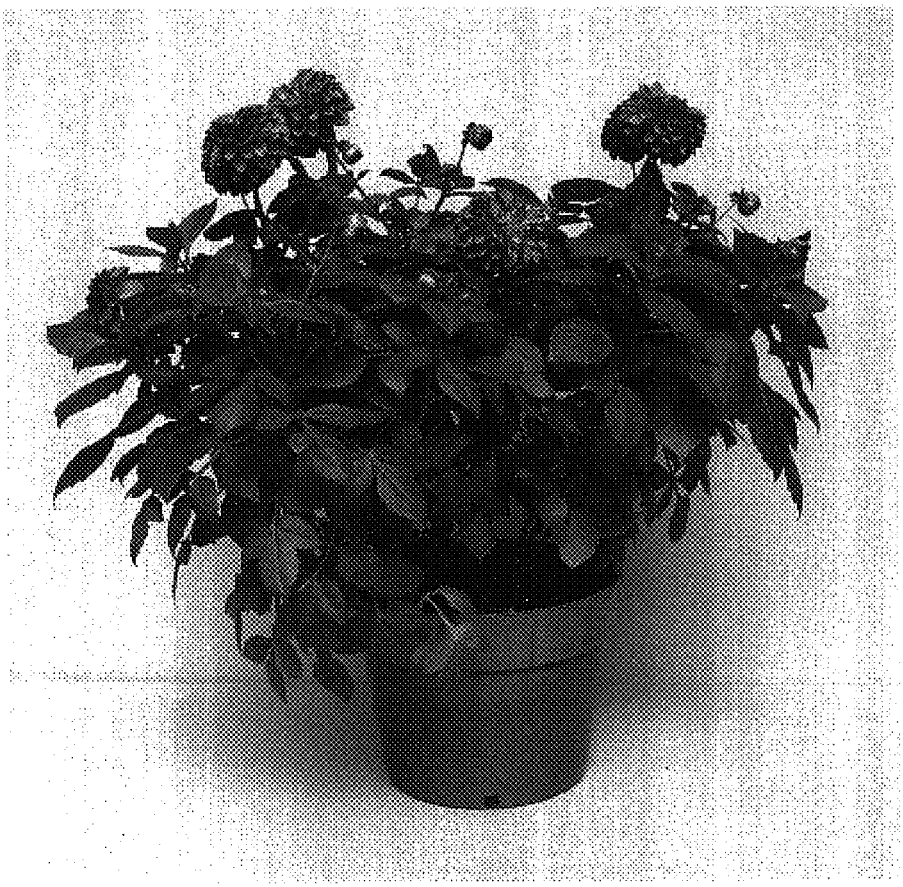
FIG. 1 illustrates a side view of the overall growth and flowering habit of 'Baldelhon'.
Figure 2:
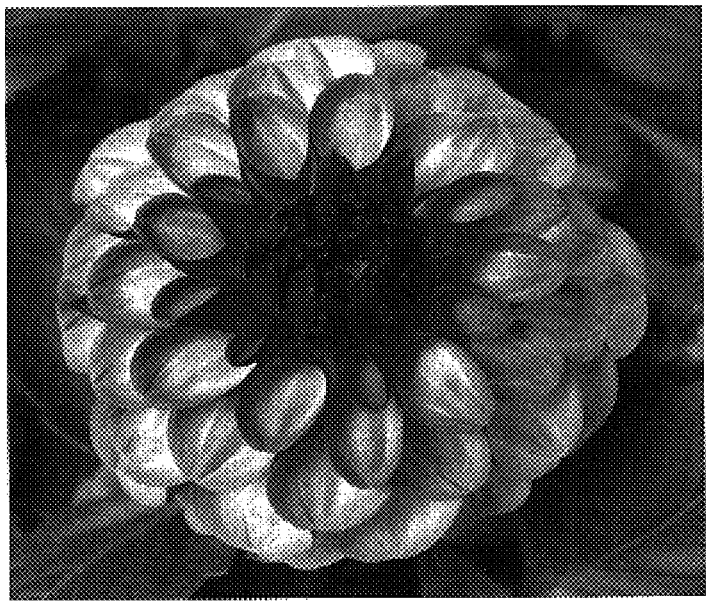
FIG. 2 illustrates a close-up view of a single inflorescence of 'Baldelhon' with open ray florets and unopened disc florets.
Figure 3:
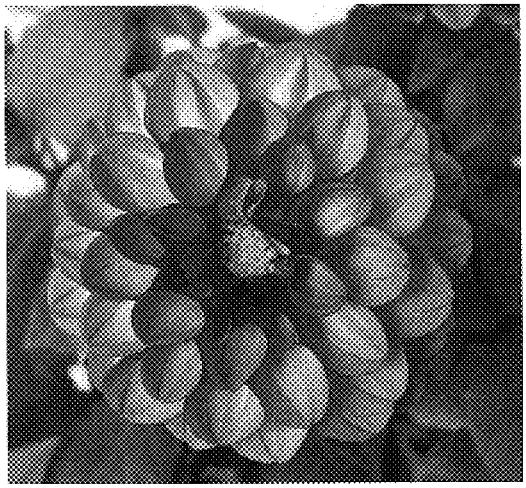
FIG. 3 illustrates a close-up ventral view of a single inflorescence of 'Baldelhon' with fully open ray florets and unopened disc florets.
Figure 4:
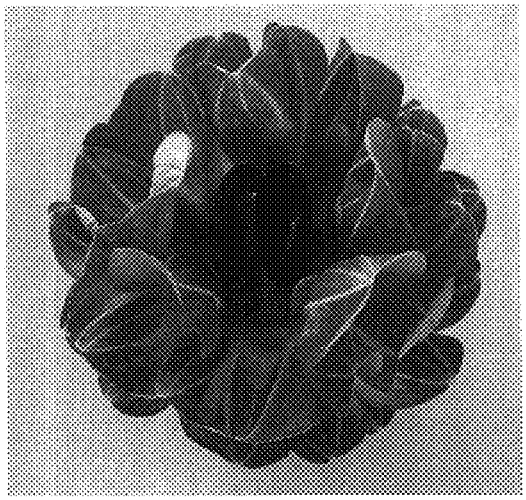
FIG. 4 illustrates a close-up dorsal side view of the same inflorescence of 'Baldelhon' as in FIG. 3.
Figure 5:
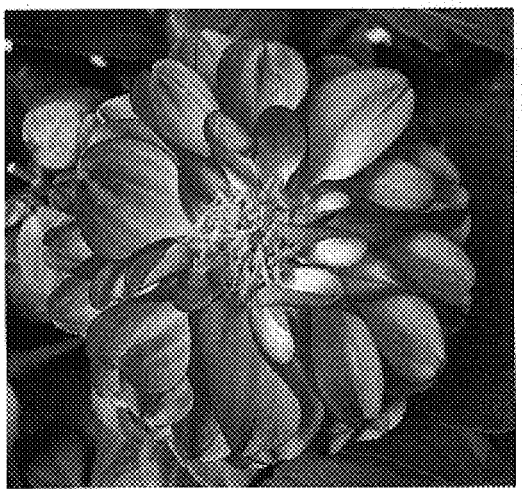
FIG. 5 illustrates a close-up view of the ventral surface of an inflorescence of 'Baldelhon' with fully open ray florets and fully open disc florets.
Figure 6:
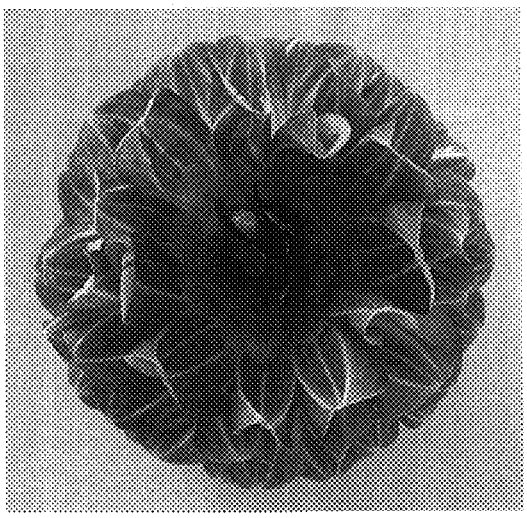
FIG. 6 illustrates a close-up dorsal side view of the same inflorescence of 'Baldelhon' as in FIG. 5 'Baldelhon'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 20, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 65° F. to 75° F. (18° C. to 24° C.) during the day and approximately 60° F. to 65° F. (15° C. to 18° C.) during the night. Greenhouse light levels of approximately 4,000 to 6,000 footcandles were maintained during the day.

Botanical classification: *Dahlia variabilis* cultivar Baldelhon.

Parentage:

*Female parent.*—Proprietary *Dahlia variabilis* breeding selection designated 1151, not patented.

*Male parent.*—'Dapasuje', not patented (concurrent application).

Propagation:

*Type cutting.*—Terminal stem.

*Time to initiate roots.*—Approximately 7 to 10 days.

*Time to produce a rooted cutting.*—Approximately 21 to 28 days.

*Root description.*—Fine, fibrous.

*Rooting habit.*—Freely branching.

*Tubers.*—Will form under short day conditions of at least 13 to 14 hours of darkness.

Plant description:

*Crop time.*—Approximately 6 to 8 weeks from a rooted cutting.

*Growth habit.*—Basal branching; pinching enhances branching.

*General appearance.*—Moderately vigorous, upright.

*Size.*—Height from soil level to top of plant plane: Approximately 24.4 cm. Height from top of soil to top of foliage: 15.6 cm. Width: Approximately 23.4 cm.

*Branch.*—Quantity per plant: Approximately 4. Strength: Strong. Length: Approximately 9.5 cm. Diameter: Approximately 5.7 mm. Texture: Glabrous. Color: Closest to 144A. Internode length at center of branch: Approximately 1.8 cm.

*Foliage.*—Quantity of leaves per lateral branch: Approximately 21. Type: Simple and compound leaves. Quantity of leaflets per compound leaf; 3. Fragrance: None. Arrangement: Opposite. Aspect: At acute angle to stem. Shape of leaf and leaflet: Elliptic. Apex of leaf and leaflet: Acute. Base of leaf and leaflet: Attenuate. Margin of leaf and leaflet: Widely dentate. Venation pattern: Pinnate. Color of upper surface of all leaves and leaflets: Darker than 137A with venation of 146C. Color of lower surface of all leaves and leaflets: Lighter than N138B with venation of 146C. Texture of upper and lower surface of all leaves and leaflets: Sparsely pubescent, with denser pubescence along veins. Length of simple leaf: Approximately 6.1 cm. Width of simple leaf: Approximately 4.8 cm. Length of petiole of simple leaf: Approximately 3.5 cm. Diameter of petiole of simple leaf: Approximately 3.0 mm. Texture of upper surface of petiole of simple leaf: Puberulent. Texture of lower surface of petiole of simple leaf: Glabrous. Color of upper surface of petiole of simple leaf: 146B. Color of lower surface of petiole of simple leaf: 146C. Length of mature trifoliate leaf: Approximately 7.2 cm. Width of mature trifoliate leaf: Approximately 7.5 cm. Length of petiole of mature trifoliate leaf: Approximately 3.1 cm. Diameter of petiole of mature trifoliate leaf: Approximately 2.7 mm. Texture of upper surface of petiole of mature trifoliate leaf: Puberulent. Texture of lower surface of petiole of mature trifoliate leaf: Glabrous. Color of upper surface of petiole of mature trifoliate leaf: Closest to 146D with overlay of 187A. Color of lower surface of petiole of mature trifoliate leaf: Closest to 146D. Length of terminal leaflet: Approximately 5.9 cm. Width of terminal leaflet: Approximately 3.8 cm. Length of rachis of terminal leaflet: Approximately 1.1 cm. Diameter of rachis of terminal leaflet: Approximately 3.1 mm. Texture of upper surface of rachis of terminal leaflet: Puberulent. Texture of lower surface of rachis of terminal leaflet: Glabrous. Color of upper surface of rachis of terminal leaflet: 146B. Color of lower surface of rachis of terminal leaflet: 146C. Length of lateral leaflet: Approximately 4.4 cm. Width of lateral leaflet: Approximately 2.6 cm.

Flowering description:

*Flowering habit.*—'Baldelhon' is freely flowering under outdoor growing conditions with substantially continuous blooming from spring through autumn and year round in greenhouse environment.

*Time to first flower.*—Approximately 14 weeks from sticking of unrooted cutting.

*Lastingness of individual bloom.*—Approximately 4 weeks.

Inflorescence description:

*Appearance.*—Type: Composite. Aspect: Facing upward and slightly outward. Arrangement: Terminal, arising from leaf axils on strong peduncles, positioned over the foliage. Disc and ray florets arranged acropetally on a capitulum. Persistant.

*Quantity per plant.*—Approximately 2 fully open at 9 weeks.

*Fragrance.*—None.

*Peduncle.*—Strength: Strong. Aspect: Erect. Length: Approximately 7.0 cm. Diameter: Approximately 2.7 mm. Texture: Glabrous. Color: 144A.

*Shape/size.*—Hemispherical when ray florets are fully open. Diameter: Approximately 6.9 cm. Depth: Approximately 4.1 cm. Disc diameter: Approximately 1.4 cm. Receptacle diameter: Approximately 9.6 mm. Receptacle height/depth: Approximately 4.0 mm. Receptacle color: 145A.

*Bud rate of opening.*—Generally takes approximately 2 weeks for bud to progress from first color to fully open inflorescence.

*Bud just before opening.*—Quantity per plant: Approximately 4 showing color at any one time. Shape: Round, flattened. Depth: Approximately 1.6 cm. Diameter: Approximately 2.0 cm. Texture: Glabrous. Color: 187C.

*Ray florets.*—Quantity: Approximately 59 per inflorescence. Arrangement: Imbricate, in several whorls. Aspect: Cupped with three ribs. Shape: Elliptic. Apex: Emarginate with three acute tips. Base: Attenuate, fused to form tube. Margin: Entire. Appearance of upper surface: Velvety. Length: Approximately 3.5 cm. Width: Approximately 1.8 cm. Texture of upper and lower surfaces: Glabrous. Color of upper surface when just opening: Between N167A and N167B. Color of lower surface when just opening: 53A. Color of upper surface when fully open: 167A at apex, transitioning to 5A at base. Color of lower surface when fully open: Between 35A and 35B at apex, transitioning to 5B at base with ridges of 5C. Color of upper surface just before senescence: 164C at apex, transitioning to 4A at base. Color of lower surface just before senescence: 53D at apex, transitioning to 5C at base.

*Disc florets.*—Quantity: Approximately 44. Arrangement: Massed in center of inflorescence. Shape: Tubular. Apex: 5 acute tips. Base: Fused. Margin: Entire. Length: Approximately 1.4 cm. Diameter at apex: Approximately 2.6 mm. Diameter at base: Approximately 1.5 mm. Texture: Glabrous. Color: 6B, transparent.

*Inner phyllaries.*—Quantity: One per floret. Shape: Linear, slightly overlapping. Apex: Acute. Base: Truncate. Margin: Entire. Length of phyllaries of outermost florets: Approximately 1.7 cm. Width of phyllaries of outermost florets: Approximately 6.6 mm. Length of phyllaries of innermost florets: Approximately 1.1 cm. Width of phyllaries of innermost florets: Approximately 4.1 mm. Texture of upper and lower surfaces: Glabrous. Color of upper and lower surfaces: 145B with 143A at base.

*Outer phyllaries.*—Quantity: Approximately 8. Shape: Rhomboidal. Apex: Cuspidate. Base: Attenuate. Margin: Entire. Aspect: Pointing downward. Length: Approximately 1.1 cm. Width: Approximately 6.0 mm. Texture of upper and lower surfaces: Glabrous. Color of upper and lower surfaces: 137A.

*Reproductive organs.*—Androecium: On disc florets. Stamen number: 5. Anther shape: Linear. Anther length: Approximately 4.0 mm. Anther color: 14A. Pollen amount: Abundant. Pollen color: 17A. Gynoecium: On disc and ray florets. Pistil length: Approximately 1.7 cm. Stigma shape: Feather. Stigma length: Approximately 4.0 mm. Stigma color: 14B. Style length: Approximately 1.3 cm. Style color: 1B. Ovary diameter: Approximately 1.5 mm. Ovary color: 150D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelhon', substantially as herein shown and described.

* * * * *